United States Patent [19]

Yamachika et al.

[11] Patent Number: 4,500,721

[45] Date of Patent: Feb. 19, 1985

[54] PROCESS FOR PRODUCING BENZALDEHYDES

[75] Inventors: Hiroshi Yamachika; Hirotoshi Nakanishi, both of Osaka, Japan

[73] Assignee: Sumitomo Chemical Company Limited, Osaka, Japan

[21] Appl. No.: 468,909

[22] Filed: Feb. 23, 1983

[30] Foreign Application Priority Data

Feb. 23, 1982 [JP] Japan ................................ 57-28264
Feb. 24, 1982 [JP] Japan ................................ 57-29181

[51] Int. Cl.³ .............................................. C07C 45/44
[52] U.S. Cl. ................................... 549/362; 560/130; 562/459; 568/436
[58] Field of Search ...................... 568/436; 549/362; 560/130; 562/459

[56] References Cited

U.S. PATENT DOCUMENTS 4,383,949 5/1983 Maurer et al. ................. 568/436 X

OTHER PUBLICATIONS

Rappoport, The Chemistry of the Cyano Group, (1970), 307–313, 319–325, 337–340.

Backeberg et al, Jour. Chem. Soc., (London), 1962, 3961–3963.

*Primary Examiner*—Bernard Helfin
*Attorney, Agent, or Firm*—Sughrue, Mion, Zinn, Macpeak and Seas

[57] ABSTRACT

A process for producing benzaldehydes by catalytic reduction of benzonitriles in the presence of an acid using a Raney nickel catalyst pretreated with a copper salt is disclosed.

11 Claims, No Drawings

PROCESS FOR PRODUCING BENZALDEHYDES

FIELD OF THE INVENTION

The present invention relates to a process for producing benzaldehydes by reduction of benzonitriles.

BACKGROUND OF THE INVENTION

Benzaldehydes have important applications in industry, and two processes are known for producing such benzaldehydes from benzonitriles. One of them is disclosed in Japanese Patent Publication No. 6326/66 and it consists of catalytic reduction of benzonitriles in the presence of lead or lead ions in an acid solvent using a Raney nickel catalyst. But the yield of benzaldehydes produced by this method is not necessarily high. The other process is described in P. Tinapp, *Chem. Ber.*, 102, 2770 (1969) and consists of catalytic reduction of benzonitriles in the presence of a Raney nickel catalyst in a mixed solvent of tetrahydrofuran and water. But this method also has low benzaldehyde yields due to the production of by-products such as benzyl alcohol and benzylamine.

SUMMARY OF THE INVENTION

As a result of various studies to find an economical process for producing benzaldehyes from benzonitriles, the present inventors accomplished the present invention which is characterized by catalytic reduction of benzonitriles in the presence of an acid using a Raney nickel catalyst pretreated with a copper salt.

DETAILED DESCRIPTION OF THE INVENTION

An important feature of the present invention is to use a Raney nickel as a reducing catalyst after it has been treated with a copper salt.

Illustrative methods of preparing the catalyst of the invention are as follows:

1. When a Raney nickel catalyst is developed by conventional manners, a copper salt is added to the catalyst.
2. A developed Raney nickel catalyst is suspended in an aqueous solution of copper salt, and the catalyst is then recovered.
3. A developed Raney nickel catalyst is reacted with a copper salt in a reaction solvent prior to reduction.

In the above described preparations, the copper content of the Raney nickel catalyst can be freely controlled by changing the proportions of the catalyst to the copper salt. For the purpose of the present invention, however, the catalyst preferably contains 5 to 80 wt%, more preferably 10 to 60 wt%, of copper. There is no limitation on the amount of the catalyst used, but to shorten the reaction time and increase the yield of the end product, 1 to 20 wt% of the catalyst is preferably used in an amount of benzonitriles.

Any inorganic or organic copper salts which are soluble in water or the reaction solvent are useful as the copper salt used in the present invention. The copper can be monovalent, divalent, or trivalent. Further, the copper salt can be an anhydrous or hydrated salt of copper. Specific examples of the copper salt include copper (II) sulfate, copper (II) chloride, copper (II) nitrate, copper (I) sulfate, copper (I) chloride, copper (I) nitrate, copper (II) acetate, copper (II) oxalate, copper (II) formate, copper (I) acetate, and the like.

The solvent used in the present invention can be widely selected from water, water-soluble organic solvents, and mixed solvents of water and water-soluble organic solvents. Illustrative water-soluble organic solvents include methanol, ethanol, propanol, tetrahydrofuran (THF), dioxane, and the like. The mixed solvent of water and organic solvents referred to herein means one containing at least 5 wt% of water. Examples of the acid that is used in the present invention include organic acids such as acetic acid, formic acid, propionic acid, tartaric acid, etc. as well as inorganic acids such as sulfuric acid, phosphoric acid, etc. To obtain benzaldehydes in high yield, the combination of solvents and acids is preferred. When water-soluble organic solvents are used alone, they are preferably combined with strong inorganic acids such as sulfuric acid, phosphoric acid, etc., which are used in an amount of 0.2 to 5 mols, preferably 0.5 to 2 mols, per mol of the starting benzonitrile. When the solvent is water or its mixture with water-soluble organic solvents, organic acids such as acetic acid, formic acid, etc. are preferably used, and the best results are obtained if their concentration in water or mixed solvent is between about 30 and 95%.

There is no particular limitation on the reduction temperature, but when it exceeds 50° C., the yield of benzaldehyde is decreased, and if the temperature is below 10° C., it takes an undesirably longer time to complete the reduction. Hence, a temperature range of from 10° to 50° C. is recommended. There is also no particular limitation on the pressure of hydrogen used as a reducing gas, but generally, the hydrogen pressure is not more than 20 kg/cm$^2$.

The starting compound for the process of the present invention is a benzonitrile compound such as benzonitrile or substituted benzonitrile wherein benzonitrile is substituted by a lower alkyl group, an oxy group, an alkoxy group, an aryl group, an aryloxy group, a carboxyl group, an acyl group, a halogen atom, a sodium sulfonate group, etc. The number of the substituents on the aromatic ring is from 1 to 5, and preferably 1 to 2. Typical examples of the starting compound include benzonitrile, o-, m- or p-tolylnitrile, p-isopropylbenzonitrile, p-t-butylbenzonitrile, p-cyanophenol, o-, m- or p-methoxybenzonitrile, o-, m- or p-phenylbenzonitrile, o-, m- or p-phenoxybenzonitrile, 3,4-dimethoxybenzonitrile, 3,4-ethylenedioxybenzonitrile, o-, m- or p-caroboxybenzonitrile, o-, m- or p-acetoxybenzonitrile, o-, m- or p-chlorobenzonitrile, and the like.

The catalyst used in the process of the present invention can be prepared in the following manner. A commercially available developed Raney nickel is dissolved in an aqueous solution of a suitable concentration of copper salt under stirring, and the resulting catalyst is then recovered and washed thoroughly with the solvent selected for use in the catalytic reduction of benzonitriles. The treatment with the copper salt is preferably conducted in an oxygen-free atmosphere.

The present invention is now described in greater detail by reference to the following examples which are given here for illustrative purposes only and are by no means intended to limit the scope of the invention.

EXAMPLE 1

(1) 9 g (wet weight) of a commercially available developed Raney nickel was added to 300 ml of a 1% CuSO$_4$.5H$_2$O aqueous solution, and the mixture was stirred for 30 minutes in a nitrogen gas stream. The color of the Raney nickel changed from black to brown.

The Raney nickel was collected by filtration and washed with ion-exchanged water to obtain 10.8 g (wet weight) of a copper salt-treated Raney nickel catalyst.

(2) To 50 g of methanol were added under stirring 5.40 g (0.0406 mol) of p-methoxybenzonitrile and 4.1 g of concentrated sulfuric acid. To the resulting solution was added 0.5 g of the copper salt-treated Raney nickel catalyst obtained in (1) above that had been thoroughly washed with methanol. The mixture was then subjected to reduction at room temperature (i.e., 22° to 24° C.) under atmospheric pressure. In 9 hours and 40 minutes, 0.0444 mol of hydrogen was absorbed.

Water (200 g) was added to the reaction solution, and the catalyst was collected by filtration and washed with 100 g of water and 50 g of ethylene dichloride. The mother liquor was combined with the washings, and further mixed with 100 g of ethylene dichloride. The mixture was allowed to stand, and the ethylene dichloride phase was separated. The aqueous phase was extracted twice with 150 g of ethylene dichloride. The ethylene dichloride phases were combined, washed with 100 g of water and concentrated to obtain 5.33 g of an oil with a p-methoxybenzaldehyde content of 95.4%. The yield was 92.1%.

EXAMPLE 2

To 50 g of ethanol were added under stirring 6.40 g (0.0403 mol) of p-t-butylbenzonitrile and 4.1 g of concentrated sulfuric acid. To the resulting solution was added 0.5 g of the copper-salt-treated Raney nickel catalyst obtained in Example 1-(1). The mixture was then subjected to reduction at 18° to 22° C. and at a hydrogen pressure of 2 kg/cm$^2$. In 11 hours, 0.0404 mol of hydrogen was absorbed. The reaction mixture was subsequently treated as in Example 1-(2) to obtain 6.46 g of an oil with a p-t-butylbenzaldehyde content of 94.8%. The yield was 93.8%.

EXAMPLE 3

To 50 g of methanol were added under stirring 10.00 g (0.0513 mol) of m-phenoxybenzonitrile and 5.1 g of concentrated sulfuric acid. To the resulting solution was added 0.5 g of the copper salt-treated Raney nickel catalyst obtained in Example 1-(1). The mixture was then subjected to reduction at 30° C. under atmospheric pressure. In 14 hours, 0.0560 mol of hydrogen was absorbed. The reaction mixture was subsequently treated as in Example 1-(2) to obtain 10.48 g of an oil with an m-phenoxybenzaldehyde content of 95.2%. The yield was 98.2%.

EXAMPLE 4

To 50 g of tetrahydrofuran were added under stirring 0.5 g (wet weight) of a developed Raney nickel catalyst and 0.3 g of copper (II) acetate. To the resulting solution were added under stirring 6.0 g (0.0368 mol) of 3.4-dimethoxybenzonitrile and 4.2 g of concentrated sulfuric acid. The mixture was then subjected to reduction at 40° C. and at a hydrogen pressure of 2 kg/cm$^2$. In 5 hours, 0.410 mol of hydrogen was absorbed. The reaction mixture was subsequently treated as in Example 1-(2) to obtain 5.99 g of an oil with a 3,4-dimethoxybenzaldehyde content of 91.3%. The yield was 89.4%.

EXAMPLE 5

To 50 g of dioxane were added under stirring 5.50 g (0.0400 mol) of p-chlorobenzonitrile and 4.0 g of concentrated sulfuric acid. To the resulting solution was added 0.5 g of the copper salt-treated Raney nickel catalyst obtained in Example 1-(1). The mixture was then subjected to reduction at 35° C. under atmospheric pressure. In 7 hours, 0.0420 mol of hydrogen was absorbed. The reaction mixture was subsequently treated as in Example 1-(2) to obtain 5.66 g of an oil with a p-chlorobenzaldehyde content of 93.0%. The yield was 93.7%.

EXAMPLE 6

1.0 g of the copper salt-treated Raney nickel catalyst obtained in Example 1-(1) was added to a solution of 6.10 g (0.0459 mol) of p-methoxybenzonitrile, 45 g of acetic acid and 5 g of water. The mixture was subjected to reduction at room temperature (i.e., 18° to 22° C.) under atmospheric pressure. In 10 hours, 0.0490 mol of hydrogen was absorbed. Water (200 g) was added to the reaction solution, and the catalyst was collected by filtration and washed with 100 g of water and 50 g of ethylene dichloride. The mother liquor was combined with the washings, and further mixed with 100 g of ethylene dichloride. The mixture was allowed to stand, and the ethylene dichloride phase was separated. The aqueous phase was extracted twice with 150 g of ethylene dichloride. The ethylene dichloride phases were combined, washed with 100 g of water and concentrated to obtain 6.14 g of an oil with a p-methoxybenzaldehyde content of 89.7%. The yield was 88.2%.

EXAMPLE 7

To a solution of 5.70 g (0.0480 mol) of p-cyanophenol, 35 g of acetic acid and 15 g of water was added 0.5 g of the copper salt-treated Raney nickel catalyst obtained in Example 1-(1). The resulting mixture was subjected to reduction at 30° C. and at a hydrogen pressure of 2 kg/cm$^2$. In 4 hours, 0.0520 mol of hydrogen was absorbed. The reaction mixture was subsequently treated as in Example 6 to obtain 5.72 g of an oil with a p-oxybenzaldehyde content of 93.1%. The yield was 91.0%.

EXAMPLE 8

To a solution of 6.30 g (0.0396 mol) of p-t-butylbenzonitrile, 20 g of acetic acid, 20 g of methanol and 10 g of water was added 0.5 of the copper salt-treated Raney nickel catalyst obtained in Example 1-(1). The resulting mixture was subjected to reduction at room temperature (i.e., 20° to 22° C.) under atmospheric pressure. In 12 hours, 0.0390 mol of hydrogen was absorbed. The reaction mixture was subsequently treated as in Example 6 to obtain 6.26 g of an oil with a p-t-butylbenzaldehyde content of 94.2%. The yield was 91.9%.

While the invention has been described in detail and with reference to specific embodiments thereof, it will be apparent to one skilled in the art that various changes and modifications can be made therein without departing from the spirit and scope thereof.

What is claimed is:

1. A process for producing a benzaldehyde by catalytic reduction using hydrogen gas of a benzonitrile in a water-soluble organic solvent in the presence of an inorganic acid using a Raney nickel catalyst pretreated with a copper salt.

2. A process for producing a benzaldehyde by catalytic reduction using hydrogen gas of a benzonitrile in water in the presence of an organic acid using a Raney nickel catalyst pretreated with a copper salt.

3. A process for producing a benzaldehyde by catalytic reduction using hydrogen gas of a benzonitrile in a mixed solvent of water and a water-soluble organic solvent in the presence of an organic acid using a Raney nickel catalyst pretreated with a copper salt.

4. A process according to claim 3, wherein said mixed solvent contains at least 5 wt% of water.

5. A process according to claim 1 or 3 wherein said water-soluble organic solvent is selected from methanol, ethanol, propanol, tetrahydrofuran and dioxane.

6. A process according to claim 1, wherein said inorganic acid is selected from sulfuric acid and phosphoric acid.

7. A process according to claim 1, wherein said inorganic acid is used in an amount of 0.2 to 5 mols per mol of said benzonitrile.

8. A process according to claim 2 or 3, wherein said organic acid is selected from acetic acid, formic acid, propionic acid and tartaric acid.

9. A process according to claim 2, wherein said organic acid is used in a concentration of from 30 to 95 wt% as a solution in water as the solvent.

10. A process according to claim 3, wherein said organic acid is used in a concentration of from 30 to 95 wt% as a solution in said mixed solvent of water and water-soluble organic solvent as the solvent.

11. A process according to claim 1, 2 or 3 wherein the catalytic reduction is effected at a temperature between 10° and 50° C.

* * * * *